(12) United States Patent
Qwarnstrom et al.

(10) Patent No.: US 9,463,046 B2
(45) Date of Patent: Oct. 11, 2016

(54) IMPLANTS AND METHODS FOR USING SUCH IMPLANTS TO FILL HOLES IN BONE TISSUE

(75) Inventors: Bo Qwarnstrom, Ferney-Voltaire (FR); Thomas Engstrand, Uppsala (SE)

(73) Assignee: OSSDSIGN AB, Uppsala (SE)

(*) Notice: Subject to any disclaimer, the term of this patent is extended or adjusted under 35 U.S.C. 154(b) by 231 days.

(21) Appl. No.: 13/214,441

(22) Filed: Aug. 22, 2011

(65) Prior Publication Data
US 2013/0053900 A1    Feb. 28, 2013

(51) Int. Cl.
*A61B 17/68*    (2006.01)
*A61F 2/28*    (2006.01)
*A61F 2/30*    (2006.01)
*A61B 17/84*    (2006.01)

(52) U.S. Cl.
CPC ........... *A61B 17/688* (2013.01); *A61F 2/2875* (2013.01); *A61B 17/842* (2013.01); *A61F 2/3094* (2013.01); *A61F 2002/285* (2013.01); *A61F 2002/2878* (2013.01); *A61F 2002/30576* (2013.01); *A61F 2002/30578* (2013.01); *A61F 2002/30878* (2013.01); *A61F 2002/30957* (2013.01); *A61F 2310/00353* (2013.01)

(58) Field of Classification Search
CPC ..................... A61F 2/2875; A61F 2002/2889; A61F 2002/285; A61F 2002/30578; A61F 17/688
USPC ............................................ 623/17.19, 23.56
See application file for complete search history.

(56) References Cited

U.S. PATENT DOCUMENTS

| | | |
|---|---|---|
| 4,905,679 A | 3/1990 | Morgan |
| 5,152,836 A | 10/1992 | Hirano et al. |
| 5,201,737 A | 4/1993 | Leibinger et al. |
| 5,338,356 A | 8/1994 | Hirano et al. |
| 5,368,602 A | 11/1994 | De la Torre |
| 5,468,242 A | 11/1995 | Reisberg |
| 5,503,164 A * | 4/1996 | Friedman ............ 128/898 |
| 5,605,713 A | 2/1997 | Boltong |
| 5,683,667 A | 11/1997 | Fulmer et al. |
| 5,690,631 A | 11/1997 | Duncan et al. |
| 5,752,958 A | 5/1998 | Wellisz |
| 5,766,176 A | 6/1998 | Duncan |
| 5,782,971 A | 7/1998 | Constantz et al. |

(Continued)

FOREIGN PATENT DOCUMENTS

| | | |
|---|---|---|
| CN | 1919357 A | 2/2007 |
| CN | 101360461 A | 2/2009 |

(Continued)

OTHER PUBLICATIONS

Bohner et al, J. Biomaterials, 26(33):6423-6429 (2005).

(Continued)

*Primary Examiner* — Bruce E Snow
*Assistant Examiner* — Melissa Hoban
(74) *Attorney, Agent, or Firm* — Porter Wright Morris & Arthur LLP (57) ABSTRACT

An implant includes a single moulded implant body and a plurality of wire anchoring arms moulded into and extending substantially laterally from the moulded ceramic implant body for filling a bore hole in a skull. The implant will not only provide filling of the bone defect, but also provide fixation of the bone flap. Methods for forming such implants and methods for using the implants for filing a bore hole in a skull are described.

38 Claims, 7 Drawing Sheets

(56) References Cited

U.S. PATENT DOCUMENTS

| | | |
|---|---|---|
| 5,783,217 A | 7/1998 | Lee et al. |
| 5,980,540 A | 11/1999 | Bruce |
| 5,984,925 A | 11/1999 | Apgar |
| 6,093,188 A | 7/2000 | Murray |
| 6,117,456 A | 9/2000 | Lee et al. |
| 6,206,957 B1 | 3/2001 | Wenz et al. |
| 6,338,810 B1 | 1/2002 | Carpena |
| 6,521,246 B2 | 2/2003 | Sapieszko et al. |
| 6,642,285 B1 | 11/2003 | Bohner et al. |
| 6,733,582 B1 | 5/2004 | Bohner et al. |
| 6,863,899 B2 | 3/2005 | Koblish et al. |
| 6,905,516 B1 | 6/2005 | Lemaitre et al. |
| 6,991,803 B2 | 1/2006 | Sapieszko et al. |
| 7,118,705 B2 | 10/2006 | Lin |
| 7,175,858 B2 | 2/2007 | Constantz et al. |
| 7,252,841 B2 | 8/2007 | Constantz et al. |
| 7,318,841 B2 | 1/2008 | Tofighi et al. |
| 7,351,280 B2 | 4/2008 | Khairoun et al. |
| 7,407,542 B2 | 8/2008 | Lemaitre et al. |
| 7,473,312 B2 | 1/2009 | Barralet et al. |
| 7,501,018 B2 | 3/2009 | Engqvist et al. |
| 7,655,047 B2 | 2/2010 | Swords |
| 7,754,246 B2 | 7/2010 | Moseley et al. |
| 7,833,253 B2 * | 11/2010 | Ralph ............... A61B 17/688 403/397 |
| 8,231,624 B1 | 7/2012 | Strippgen |
| 8,246,663 B2 | 8/2012 | Lovald et al. |
| 8,281,638 B2 | 10/2012 | Metzger |
| 8,298,292 B2 | 10/2012 | Swords et al. |
| 8,361,126 B2 | 1/2013 | Perrow et al. |
| 8,366,751 B2 | 2/2013 | Pfefferle |
| 2003/0082232 A1 | 5/2003 | Lee et al. |
| 2003/0199615 A1 | 10/2003 | Chaput et al. |
| 2005/0149032 A1 | 7/2005 | Vaughen et al. |
| 2006/0116682 A1 | 6/2006 | Longo |
| 2006/0239884 A1 | 10/2006 | Chane-Ching et al. |
| 2006/0263443 A1 | 11/2006 | Chow et al. |
| 2007/0092856 A1 | 4/2007 | Chow et al. |
| 2007/0173844 A1 | 7/2007 | Ralph et al. |
| 2007/0189951 A1 | 8/2007 | Constantz et al. |
| 2008/0027455 A1 | 1/2008 | Boudeville |
| 2008/0028992 A1 | 2/2008 | Lee et al. |
| 2008/0187571 A1 | 8/2008 | Clineff et al. |
| 2008/0206300 A1 | 8/2008 | Bohner et al. |
| 2009/0022771 A1 | 1/2009 | Lynn et al. |
| 2009/0076617 A1 * | 3/2009 | Ralph ............... A61B 17/688 623/17.19 |
| 2009/0220475 A1 | 9/2009 | Bohner et al. |
| 2010/0069455 A1 | 3/2010 | Takato et al. |
| 2010/0095870 A1 | 4/2010 | Insley et al. |
| 2010/0269736 A1 | 10/2010 | Chow et al. |
| 2010/0303888 A1 | 12/2010 | Barralet et al. |
| 2011/0014244 A1 | 1/2011 | Sapieszko et al. |
| 2011/0054540 A1 | 3/2011 | Ralph et al. |
| 2011/0152195 A1 | 6/2011 | O'Mahony et al. |
| 2011/0158963 A1 | 6/2011 | Font Perez et al. |
| 2012/0058152 A1 | 3/2012 | Garcia de Castro Andrews et al. |
| 2013/0138114 A1 | 5/2013 | Lin et al. |

FOREIGN PATENT DOCUMENTS

| | | |
|---|---|---|
| CN | 101528158 A | 9/2009 |
| EP | 543765 A1 | 5/1993 |
| EP | 544384 B1 | 1/1996 |
| EP | 433852 B1 | 3/1996 |
| EP | 1023032 B1 | 1/2002 |
| EP | 910993 B1 | 7/2002 |
| EP | 984745 B1 | 10/2003 |
| EP | 936929 B1 | 6/2004 |
| EP | 1380313 B1 | 5/2005 |
| EP | 1178847 B1 | 1/2007 |
| EP | 1420725 B1 | 8/2008 |
| EP | 2014258 A1 | 1/2009 |
| EP | 2030596 A1 | 3/2009 |
| EP | 1298103 B1 | 5/2011 |
| EP | 2474286 A1 | 7/2012 |
| EP | 2529702 A1 | 12/2012 |
| JP | 1-100049 A | 4/1989 |
| JP | 2006-218050 A | 8/2006 |
| JP | 2007-501054 A | 1/2007 |
| WO | 95/20368 A1 | 8/1995 |
| WO | 02/11781 A1 | 2/2002 |
| WO | 02/22045 A1 | 3/2002 |
| WO | 03/007831 A1 | 1/2003 |
| WO | 2004/093734 A2 | 11/2004 |
| WO | 2004/108019 A2 | 12/2004 |
| WO | 2004/112859 A1 | 12/2004 |
| WO | 2005/016616 A1 | 2/2005 |
| WO | 2005/074453 A2 | 8/2005 |
| WO | 2005/077049 A2 | 8/2005 |
| WO | 2005/122956 A2 | 12/2005 |
| WO | 2007/047921 A2 | 4/2007 |
| WO | 2008/002595 A2 | 1/2008 |
| WO | 2009/077210 A1 | 6/2009 |
| WO | 2010/055483 A2 | 5/2010 |
| WO | 2010/092001 A1 | 8/2010 |
| WO | 2011/009635 A1 | 1/2011 |
| WO | 2011/068451 A2 | 6/2011 |
| WO | 2011/112145 A1 | 9/2011 |
| WO | 2012/016200 A1 | 2/2012 |
| WO | 2012/103164 A1 | 8/2012 |
| WO | 2012/118843 A1 | 9/2012 |
| WO | 2012/147114 A1 | 11/2012 |

OTHER PUBLICATIONS

Xu et al, Journal of Materials Science: Materials in Medicine, 18(7):1345-1353 (2007).

Barralet et al, J. Biomaterials, 25(11):2197-2203 (2004).

Habraken et al, Advance Drug Delivery Reviews, 59(4-5):234-248 (2007).

Han et al, Acta Biomaterialia, 5:3165-3177 (2009).

Desai et al, Advances in Bioceramics and Biocomposites II, Ceramic Engineering and Science Proceedings, vol. 27, Issue 6, Wereszczak et al, Editor, Wiley, pp. 61-69 (Nov. 2006).

Hirayama et al, Journal of Research of the National Institute of Standards and Technology, 113(6):311-320 (2008).

International Search Report and Written Opinion from corresponding PCT/IB2012/054228, dated Feb. 19, 2013.

English Translations of the Search Report and Notification of the First Office Action dated Dec. 10, 2015, from the corresponding CN 2012800468932.

Official Action dated Jun. 20, 2016 from corresponding Japanese Application No. 2014-526587, and English translation of Official Action.

* cited by examiner

IMPLANTS AND METHODS FOR USING SUCH IMPLANTS TO FILL HOLES IN BONE TISSUE

FIELD OF THE INVENTION

The invention relates to surgical implants, methods for making such implants and methods for using such implants to fill holes in bone tissue.

BACKGROUND OF THE INVENTION

Craniotomy is a procedure during which a surgeon makes a bone flap and removes it temporarily to access the brain during surgery. The bone flap is formed by first drilling plurality, usually two to four, of spaced-apart bore holes though the skull of the patient and then cutting through the bone between the bore holes using a saw. At the end of the procedure, the bone flap is replace and reattached to the skull, however the bore holes seldom heal and provide no protection to the underlying brain.

Such bore holes that cannot heal can be filled using autograph, allograph or synthetic scaffold materials. Scaffold strategies involve providing metal meshes or porous ceramic materials. Current strategies using metal mesh do not induce tissue healing. Currently used ceramics are utilized only to provide osteoconductive support but will not provide fixation of the bone flap to adjacent cranial bone. Most commonly, the bore holes are left untreated.

BRIEF DESCRIPTION OF THE INVENTION

The present invention describes an implant (an implant is a kind of medical device made to replace and act as a missing biological structure), which can be used as a biomedical implant and which combines a wire or mesh anchoring system (a wire anchoring system comprises plurality of wires, preferably crossing wires, where none of the wires are joined to each other while a mesh comprises at least two crossing wires joined at some or all of their intersections) and a biomaterial mosaic element which provides increased combined bone in-growth and better mechanical properties compared to prior art systems. A biomaterial is any matter, surface, or construct that interacts with biological systems. The implant comprises a mosaic element that combines at least one flexible high strength wire or mesh with at least one mosaic tile. The invention can be employed as a replacement for the bone removed by drilling during craniotomy. The biomedical implant can be composed of resorbable biomaterials and/or stable biomaterials such as polymers, ceramics and metals. Preferably the implant is osteo-conductive (i.e. can serve as a scaffold on which bone cells can attach, migrate, and grow and divide) or osteo-inductive (i.e. can serve to induce new bone formation), and has high mechanical strength. This is satisfied by an implant system that combines an anchoring system (for example one or more wires) with a solid biomaterial tile—the implant body. Preferably the anchoring system is made of a biomaterial. This system has the beneficial effects of a mechanically strong anchoring system (e.g. a wire) and an osteo-conductive and/or osteo-inductive solid implant (e.g. made of a ceramic material). The implant system can be easily attached to a skull in the operation room. The anchoring system may be attached to adjacent cranial bone and a bone flap by screws. Alternatively the anchoring system may use anchoring channels formed in the skull and or bone flap which are positioned to receive the wires. Combinations of screws and anchoring channels are also possible. The solid implant body, which preferably is moulded onto the wire or wires during manufacturing of the implant, is preferably composed of an osteo-conductive and/or osteo-inductive material that facilitates bone in-growth onto the implant system.

Preferably the anchoring system comprises one or more wires that may be manipulated by the surgeon to match the groove in the skull. The implant body may also be flat or, preferably, it is dished to provide a better match to the curvature of a skull. In one embodiment of the present invention a biomaterial tile is moulded around the one or more wires. In this way a structure comprising a wire-supported tile is formed.

In another embodiment of the present invention the wires extend out of the implant body and then re-enter the implant body, thereby forming a closed loop which can be anchored in channels formed with a matching shape and appropriate dimensions in the bone.

Non-limiting examples of wires include polymers, shape memory alloys, Ti, Ti alloys (e.g. Ti6Al4V) and stainless steel. In the present application the word "wire" is intended to include filaments made of any such material. The biomaterials are preferably mouldable from the chemically bonded ceramic class of materials or a biopolymer, non-limiting examples include Ca-salts like: calcium sulphate, calcium phosphate, calcium silicate, calcium carbonate or combinations thereof. The materials are preferably moulded onto the wires using a non-aqueous water-miscible liquid or using a mixture of water and a non-aqueous water-miscible liquid, allowed to harden to form a mosaic implant in a water containing bath and subsequently the mosaic implant is released from the mould. After packing and sterilization the tile is ready to be used. A typical mould and manufacturing process of an implant system in accordance with an embodiment of the present invention involves the following steps:

1. Manufacture of a positive model of implant.
2. Manufacture a mould for the scaffold. The mould is preferably produced of a polymer that is easy to de-mould after setting, for example sodium alginate or polyether. One preferred mould material is silicone rubber, due to its high biocompatibility and easy handling. The model is used to manufacture the mould by applying the mould material onto the positive model and let the mould material set. Examples of suitable mould materials include: Silagum, Silagum light (DMG Dental) and Silupran 2450 (Wacker silicones). The first two are dental impression materials and the later is used for temporary implants.
3. Filling the mould with a chemically bonded ceramic precursor powder mixed with a non-aqueous water-miscible liquid and optionally water.
4. Letting the filled mould harden in a moist or wet environment, preferably in temperatures between room temperature and 120 degrees Celcius. According to one embodiment the material is set and hardened under an external pressure, e.g. using a mechanical press or the like. This produces a final product with a higher mechanical strength compared to a final product hardened in the absence of an external pressure.
5. Demoulding the sample and optionally letting the samples further harden in a moist or wet environment preferably at elevated temperatures as described below.
6. Optional soaking of the samples to remove any excess non-aqueous water-miscible liquid.
7. Optional final polishing of the samples.
8. Packing and sterilisation using conventional sterilising methods and packaging solutions.

The new implant will provide both filling of a bone defect with osteoconductive/inductive material and simultaneously provide fixation of the bone flap with the anchoring system. In a preferred embodiment of the invention the ceramic tile forming the body of the implant may be simply put into the defect and fixed with screws inserted into openings or loops in anchoring arms. Preferably two anchoring arms are attached to the bone flap and two anchoring arms are attached to adjacent bone.

DETAILED DESCRIPTION OF THE INVENTION

Figure 1:
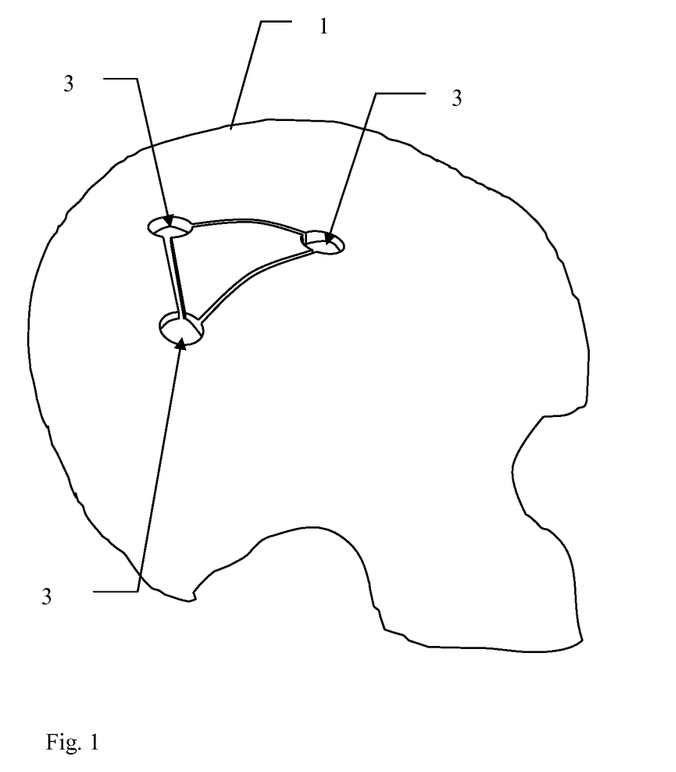
FIG. 1 shows schematically a skull with a bone flap and bore holes.

FIG. 1 shows schematically a side view of a skull 1 with three bore holes 3. The bore holes are joined by saw cuts 5 which together with the bore holes form a continuous cut line through the skull, thereby releasing a bone flap 7 from the rest of the skull. Bone flap 7 can be lifted to allow access to the underlying tissue.

When the bone flap 7 is replaced it is desirable not only to anchor it into place but also to at least partly fill the bore holes 3.

Figure 2:
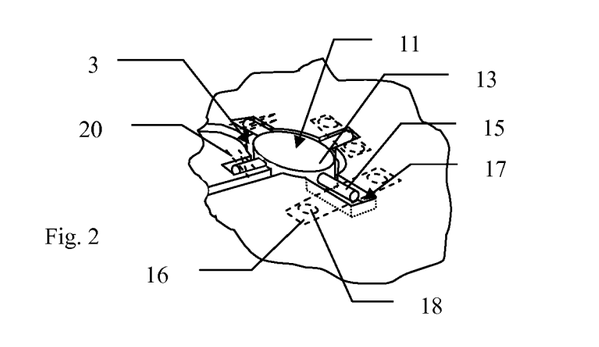
FIG. 2 shows schematically an enlarged portion of the skull shown in FIG. 1) with a bore hole plugged with an implant in accordance with the present invention.

FIG. 2 shows schematically an enlarged portion of the skull shown in FIG. 1) with a bore hole 3 plugged with an implant 11 in accordance with the present invention. Implant 11 comprises a round tile 13 and a plurality of anchoring arms 15 extending laterally from it. Other implant body shapes are also conceivable, for example, oval triangular, square, rectangular, pentagonal, hexagonal, etc, however a circular shape is preferred as it can most closely match a circular bore hole. Each arm 15 is accommodated in its own groove 17 formed in the skull. The arms are each retained in their grooves by retaining means—shown by dashed lines, for example via plates 16 and screws 18 and/or clamps and/or sutures 20 or any other fixing means.

Figure 3A:
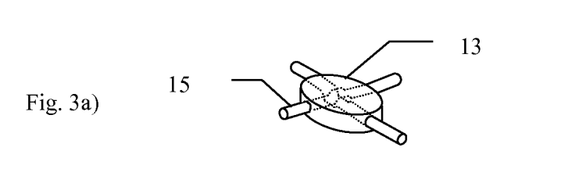
FIGS. 3a)-3c) shows schematically the implant of FIG. 2 in perspective, plan and side views.
Figures 3B, 3C:
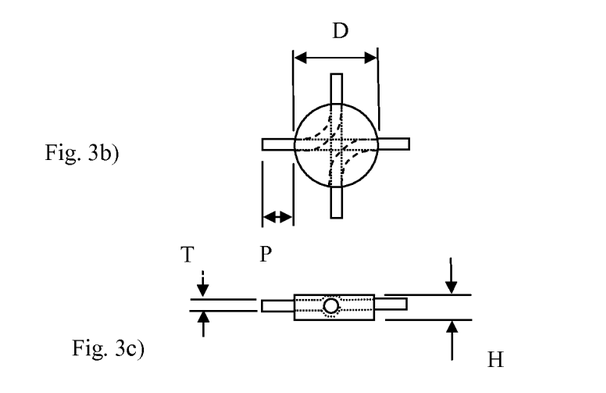

FIGS. 3a)-3c) shows schematically the implant 11 of FIG. 2 in perspective, plan and side views. Implant 11 has a circular body 13 of diameter D and height H. Preferably D is greater than H. Preferably D is between 8 and 20 mm, more preferably between 9 and 15 mm and even more preferably between 10 and 14 mm. Height H is preferably between 1 and 10 mm, more preferably between 2 and 8 mm and even more preferably between 3 and 6 mm. Protruding substantially radially from body 13 are anchoring wires 15. Each wire protrudes a distance P from body 13 and has a diameter T. Preferably the length of protrusion P is between 2 and 15 mm, more preferably between 3 and 10 mm and even more preferably between 4 and 8 mm. The diameter T of each wire is preferably less than 3 mm, more preferably less than 2 mm and most preferably 1 mm or less. In this example of the first embodiment of the invention there are four anchoring wires 15 made from two lengths of wire which cross inside the tile as shown by dotted lines in FIGS. 3a) and 3b). Instead of having crossing wires, it is conceivable to have two bent wires which do not cross, as shown by dashed lines in FIG. 3b) or to use four wires (not shown), with each wire forming an anchoring wire. Alternatively, the anchoring wires may be replaced by flat plates with a height preferably from 0.2 to 2 mm and a width preferably from 2 to 6 mm and a length which preferably from 5 to 15 mm. Each plate is provided with a through hole which allows an attachment screw to be inserted through the plate and screwed into the underlying bone. Examples of plate material are titanium or degradable polymer. Plates can be moulded into the ceramic tile and extended outside the tile laterally on a plurality of sides.

Figure 4:
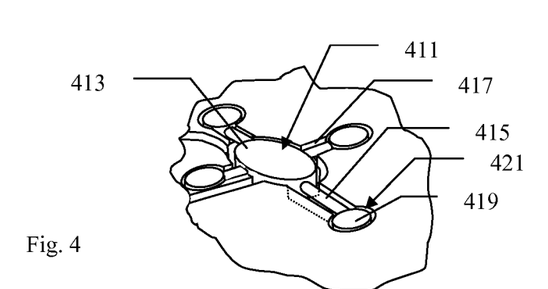
FIG. 4) shows schematically an enlarged portion of the skull shown in FIG. 1) with a bore hole plugged with an implant in accordance with a second embodiment of the present invention FIG. 5a)-5c) shows schematically the implant of FIG. 4 in perspective, plan and side views.
Figure 5A:
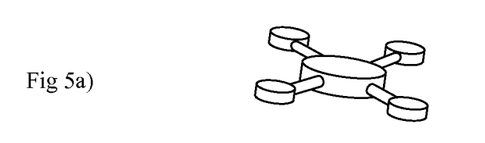
Figures 5B, 5C:
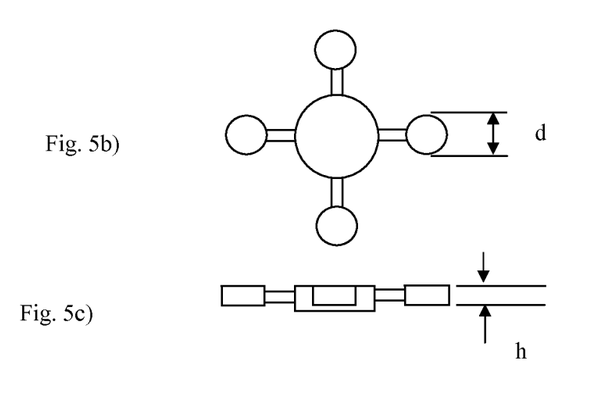

FIGS. 4 and 5a)-5c) show schematically a second embodiment of the present invention in which each anchoring wire 415 extending from the body 413 of the implant 411 is provided with a substantially circular anchoring tile 419 at its distal end. Each anchoring tile has a diameter d and a height h. Preferably d is between 2 and 10 mm, more preferably between 3 and 8 mm and even more preferably between 4 and 6 mm. Height h is preferably between 0.5 and 6 mm, more preferably between 1 and 5 mm and even more preferably between 1.5 and 4 mm. The anchoring tile is intended to be positioned in an anchoring chamber 421 formed at the end of each of the anchoring grooves 417. Preferably d is less than D and h is less than H in order to minimise the amount of material which has to be removed to form anchoring chambers. The arms and/or anchoring tiles are each retained in their grooves by retaining means—not shown—for example via plates and screws and/or clamps and/or sutures or any other fixing means.

Figure 6:
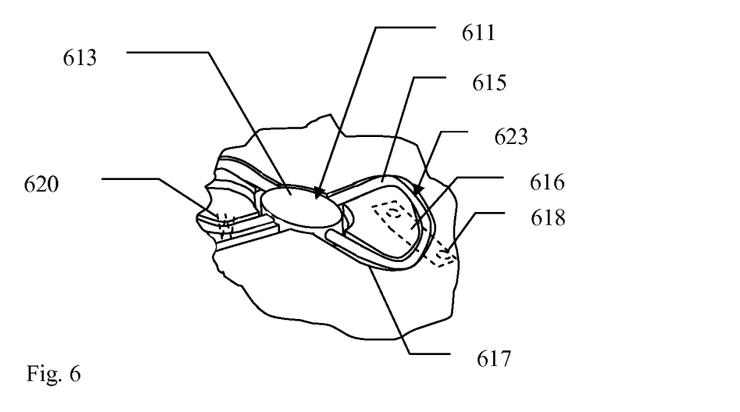
FIG. 6) shows schematically an enlarged portion of the skull shown in FIG. 1) with a bore hole plugged with an implant in accordance with a third embodiment of the present invention FIG. 7a)-7c) show schematically the implant of FIG. 6 in perspective, plan and side views, FIGS. 8a) and 8b) show schematically a fourth embodiment of an implant in accordance with the present invention, FIGS. 9a) and 9b) show schematically respectively in plan view and in section along line A-A of FIG. 9a), a mould used for making an implant in accordance with the present invention, FIG. 9c) shows in section another embodiment of a mould and a wire for making an implant in accordance with the present invention.
Figure 7A:
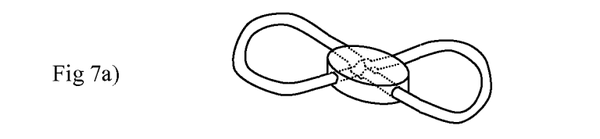
Figure 7B:
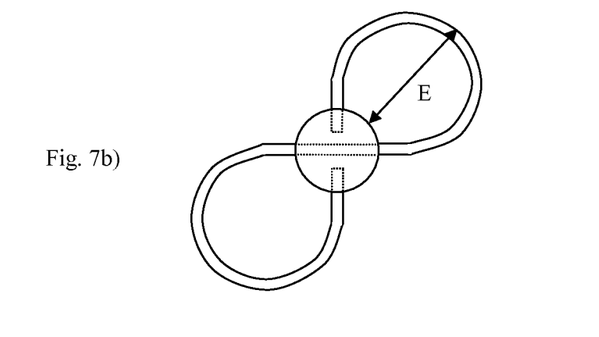
Figure 7C:
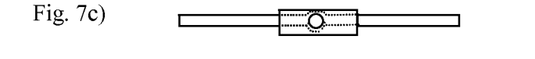

FIGS. 6 and 7a)-7c) show schematically a third embodiment of the present invention in which the anchoring wire 615 of the implant 611 forms one or more closed loops 623 protruding from the body 613 of the implant. As can be seen in FIG. 7b) a single anchoring wire is formed into a figure of eight shape with its ends almost meeting at the centre of the figure of eight shape. The body 613 of the implant is formed over these ends. The closed loops extend a distance E from the body 613. Preferably E is between 5 and 15 mm, more preferably between 6 and 12 mm and even more preferably between 8 and 10 mm. The anchoring loops are intended to be positioned in suitably formed anchoring grooves 617 which extend from a bore hole 603 and then return to the same bore hole. The arms are each retained in their grooves by retaining means—shown by dashed lines, for example via plates 616 and screws 618 and/or clamps and/or sutures 620 or any other fixing means.

Figure 8A:
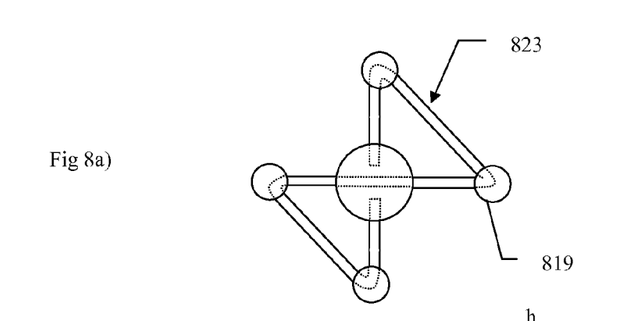
Figure 8B:
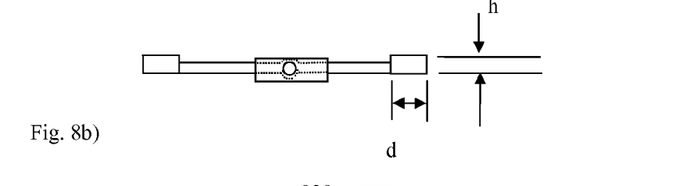

FIGS. 8a) and 8b) show schematically a fourth embodiment of the present invention in which the single anchoring wire 815 of the implant 811, in addition to being bent into a flattened figure of eight shape to form two closed loops 823, is provided with at least one (in this example two) substantially circular anchoring tiles 819 at intermediate portions of the loops. Each anchoring tile has a diameter d and a height h. Preferably d is between 2 and 10 mm, more preferably between 3 and 8 mm and even more preferably between 4 and 6 mm. Height h is preferably between 0.5 and 6 mm, more preferably between 1 and 5 mm and even more preferably between 1.5 and 4 mm. Each anchoring tile is intended to be positioned in an anchoring chamber formed at an appropriately located position in an anchoring groove (not shown). Alternatively, each anchoring tile may be provided with an opening to accept a screw which can be used instead of an anchoring groove or in addition to an anchoring groove to attach the anchoring tile to the underlying skull. The arms and/or anchoring tiles may also each retained in their grooves by retaining means—not shown—for example via plates and screws and/or clamps and/or sutures or any other fixing means.

It is conceivable to form the loops from a plurality of wires with the ends of each wire embedded in the implant body 813 and the anchoring tiles 819, however the use of a single wire is preferred as it is easier to handle.

It is of course possible to attach any anchoring means in accordance with the present invention directly to the bone flap and bone without forming anchoring channels—this may be achieved by fixing the anchoring wires or plates by suitably placed screws which clamp the anchoring wires or plates or tile between the underside of the screw and the underlying bone or bone flap, or by using sutures or any other fixing means.

An implant in accordance with the above embodiments of the present invention can be implanted in a patient by a method comprising the steps of:
i) optionally forming one or more anchoring grooves in the bone and/or bone flap surrounding a bore hole, and, if the implant comprises one or more anchoring tiles or, forming one or more anchoring chambers in the bone and/or bone flap,
ii) if necessary bending the anchoring wires to match the orientations of the one or more anchoring grooves and any anchoring chambers if anchoring grooves or anchoring chambers are present,
iii) placing the implant body in the bore hole,
iv) optionally placing the one or more anchoring wires in the one or more anchoring grooves if present and/or, if present the one or more anchoring tiles in the one or more anchoring chambers,
iv) fixing any anchoring wires or plates which are not anchored in anchoring grooves or anchoring chambers, preferably by anchoring means such as a screw or suture or the like, to the surrounding bone and to the bone flap.

Thus implants can be fixed to the bone flap and skull by anchoring means fitted and retained in anchoring grooves or channels, or by screws passing though anchoring loops or holes or by plates and screws and the like and by combinations of these methods.

Figure 9A:
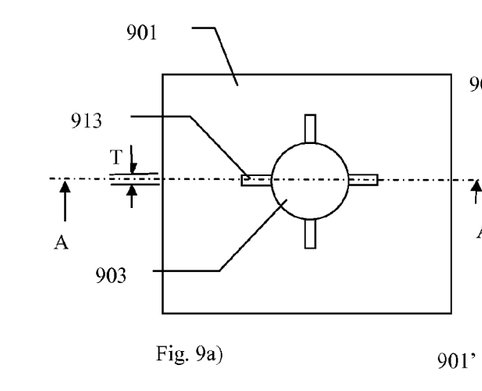
Figure 9B:
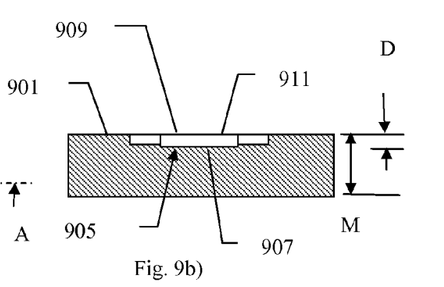
Figure 9C:
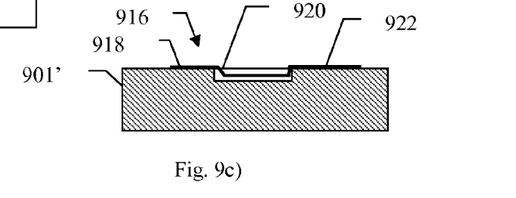

In one embodiment of a method of manufacturing a mosaic implant in accordance with the present invention a mould 901 of thickness M is used which, as shown in plan view FIG. 9a) and in FIG. 9b), as a section along line A-A of FIG. 9a), comprises at least one cavity 903 of depth H and width D. Each cavity has the shape of an implant body. The depth D of the cavities and the thickness of the resulting tile are less than the depth M of the mould. Each cavity 903 has a closed bottom end 905 which is closed by the floor 907 of the mould 901 and is open at the opposite open end 909 to allow filing of the cavity 903. Floor 907 does not have to be permanently attached to the mould but may, for example, be a surface which the mould is in contact with during manufacturing of the implant and which can be removed after moulding to facilitate release of the implant from the mould. Preferably each cavity and thus each tile subsequently formed is in the shape of a circle. However it is conceivable that the cavity and the subsequently formed implant body may have another shape such as a triangle, a square, a rectangle, a pentagon, a hexagon etc. In this embodiment of a mould, the wall 911 of each cavity 903 is pierced by at least one narrow, wire-retaining channel 913 of width T and depth which is the same as T (which is used when the top surface of the anchoring wire is to be flush with the top surface of the implant body) or greater than T (which is used when the top surface of the anchoring wire is intended to be below the top surface of the implant body). It is also possible that the depth of the wire-retaining channels is less than T in which case the upper surface of the anchoring wire will be above the top surface of the implant body. Wire-retaining channels 913 are intended to receive, and to retain during the casting process, the wires used to form the implant anchoring arrangement. In this embodiment of the invention, each cavity is only crossed by one wire in the first direction and one wire in the substantially perpendicular direction. Other arrangements such as two wires crossing at 120° or any other non-perpendicular angle are also conceivable. In another embodiment of a mould 901', shown in FIG. 9c) the wire-retaining channels are omitted and instead the wire 916 may be bent so that the portions 918 of the wire outside the cavity lay on the upper surface of the mould and extend radially away from the cavity, an intermediate portion 920 projects down into the mould cavity and the remaining portion of the wire 922 extends parallel to the top surface of the mould. The intermediate and remaining portions of the wire are subsequently covered by the cement. An implant made in this way will be able to be fitted with its top surface flush with the top surface of the bone flap and/or skull, with only the exposed portions of the wire(s) protruding above the surface of the bone flap and/or skull.

While the cavities have been shown with vertical walls 911, it is of course possible to have walls sloping such that the width across any section of the bottom closed end of each cavity is smaller than the width of the corresponding section of the open end of the cavity in order to form release slopes which aid releasing of the moulded product from the mould. An implant in accordance with the present invention can be made by placing wires in the wire-retaining channels, filing the mould with cement, allowing the cement to cure and then removing the thus formed implant from the mould.

Other moulding methods may be used to form a mosaic implant in accordance with the present invention. For example, one or more anchoring wires can be placed on the exposed surface of a first mould half comprising one or more cavities of depth less than D separated by walls. The first mould half is provided with an excess amount of cement composition which not only fills the cavities and covers the wire(s) but also extends away from the exposed surface of the first mould half. A second mould half, which preferably has cavities of depth less than D but which together with the depth of the cavities of the first mould half are equal to D. The cavities are arranged as a mirror-image of the first mould half, and the second mould half is subsequently put on top of the wire and compressed toward the bottom mould to allow moulding of implant bodies around the wires. The excess amount of cement composition should be sufficient to fill the cavities in the second mould half and should be positioned to be able to fill the second mould half. Excess cement is removed after the mould halves have been united and preferably before hardening of the cement. Hardening of the cement may be achieved by adding moisture via holes each hole being connected to each moulding cavity within the mould. Such holes preferably are dimensioned so that they are also suitable for allowing excess cement to leave the mould.

Figure 10:
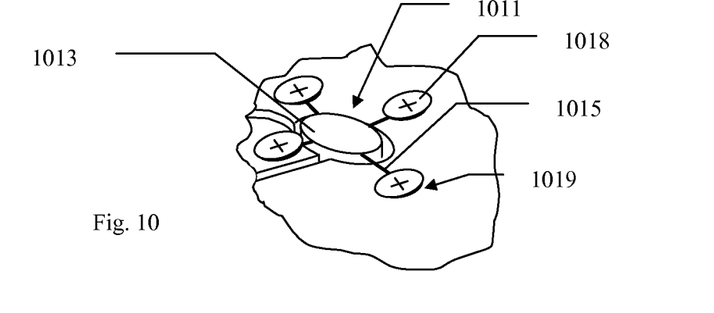
FIG. 10 shows schematically an enlarged portion of the skull shown in FIG. 1) with a bore hole plugged with an implant in accordance with a further embodiment of the present invention, FIGS. 11a)-11c) show schematically the implant of FIG. 10 in perspective, plan and side views.
Figure 11A:
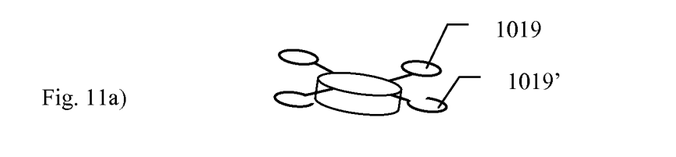
Figure 11B:
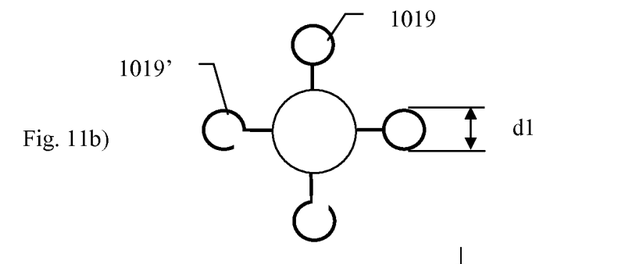
Figure 11C:
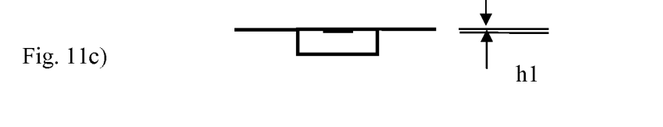

FIGS. 10 and 11a)-11c) show schematically a further embodiment of the present invention in which each anchoring wire 1015 extending from the body 1013 of the implant 1011 is provided with a substantially circular anchoring loop 1019 at its distal end. Each anchoring loop has a diameter d1 and a height h1. Preferably d1 is between 2 and 10 mm, more preferably between 3 and 8 mm and even more preferably between 4 and 6 mm. Height h1 is preferably the same as the thickness of the anchoring wire and is between 0.1 and 2 mm, more preferably between 0.25 and 1.25 mm and even more preferably between 0.3 and 0.8 mm. The anchoring loop is intended to be positioned directly on the bone or bone flap and to be retained by a screw 1018 or the like passing though the loop 1019 and into the underlying bone. Anchoring loops may be closed as shown by loops with reference number 1019 or open as shown by loops with reference number 1019'.

Figure 12:
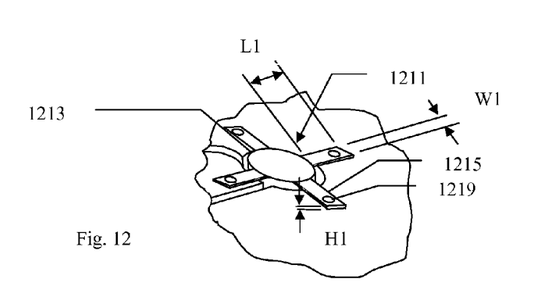
FIG. 12 shows schematically an enlarged portion of the skull shown in FIG. 1) with a bore hole plugged with an implant in accordance with a yet another embodiment of the present invention, and FIGS. 13a) and 13b) show schematically respectively in plan view and in section along line A-A in FIG. 13a) a further embodiment of a mould used for making an implant in accordance with the present invention, FIG. 13c) shows in section yet a further embodiment of a mould and a plate for making an implant in accordance with the present invention.

FIG. 12 shows schematically yet another embodiment of the present invention similar to that of FIGS. 10 and 11a) to 11c) in which the anchoring wires have been replaced by anchoring plates 1215 which extend from the body 1213 of the implant 1211. The plates have a height H1 preferably from 0.2 to 2 mm and a width W1 preferably from 2 to 6 mm and a length L1 preferably from 5 to 15 mm. Each plate is provided with a through hole which allows an attachment screw to be inserted through the plate and screwed into the underlying bone. Each plate is provided with an anchoring opening 1219 at its distal end, the opening being intended to receive a screw, suture or the like for fastening in underlying bone. Preferably the implant should have at least two anchoring means in the form of anchoring wire and/or one anchoring plates, one anchoring means being intended to be attached to the bone flap and the other for attachment to the surrounding bone. Increase stability of the implant is achieved by having three or more anchoring means.

Figure 13A:
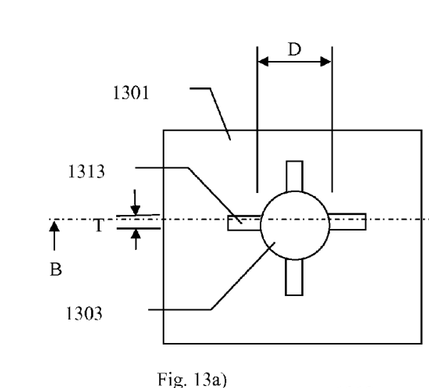
Figure 13B:
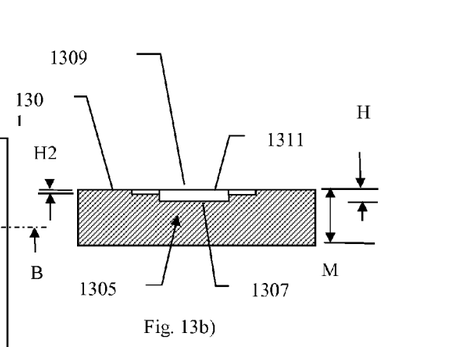
Figure 13C:
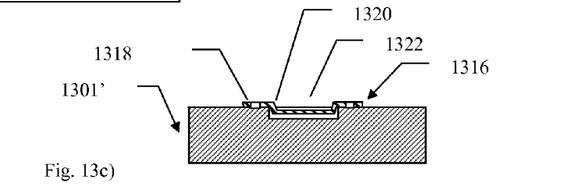

FIGS. 13a) and 13b) illustrate schematically respectively a plan view and a section along line B-B of FIG. 13a) of a mould for use in manufacturing a mosaic implant in accordance with the embodiment of the invention shown in FIG. 12. A mould 1301 of thickness M is used which, as shown in FIGS. 13a) and 13b), comprises at least one cavity 1303 of depth H and width D. Each cavity has the shape of an implant body. The depth H of the cavities and the thickness of the resulting tile is less than the depth M of the mould. Each cavity 1303 has a closed bottom end 1305 which is closed by the floor 1307 of the mould 1301 and is open at the opposite open end 1309 to allow filing of the cavity 1303. Floor 1307 does not have to be permanently attached to mould but may, for example, be a surface which the mould is in contact with during manufacturing of the implant and which can be removed after moulding to facilitate release of the implant from the mould. Preferably each cavity and thus each tile subsequently formed is in the shape of a circle. However it is conceivable that the cavity and the subsequently formed implant body may have another shape such as a triangle, a square, a rectangle, a pentagon, a hexagon etc. The wall 1311 of each cavity 1303 is pierced by at least one narrow, plate-retaining channel 1313 of width T and depth H2 which is more than, the same as or less than the thickness of the plate H1 depending on whether the upper surface of the plate is be above, level with, or below the upper surface of the implant body. These plate-retaining channels 1313 are intended to receive and to retain during the casting process the anchoring plates used to form the implant anchoring arrangement. In another embodiment of a mould 1301', shown in section in FIG. 13c) the plate-retaining channels are omitted and instead the plates 1316 may be bent so that the portions 1318 of the plate outside the cavity lay on the upper surface of the mould and extend radially away from the cavity, an intermediate portion 1320 projects down into the mould cavity and the remaining portion of the plate 1322 extends parallel to the top surface of the mould. The intermediate and remaining portions of the plate are subsequently covered by the cement while the portion of the plate outside the cavity is available for attachment to an underlying surface. An implant made in this way will be able to be fitted with its top surface flush with the top surface of the bone flap and/or skull, with only the exposed portion of the plate(s) protruding above the surface of the bone flap and/or skull.

An implant in accordance with embodiments of the present invention may be implanted in a patient by a method comprising the steps of:
1) placing the implant body in the bore hole,
2) fixing the anchoring wires or plates, preferably by screws and/or sutures or the like, to the surrounding bone and to the bone flap.

An implant in accordance with the present invention may be implanted in a patient by a further method comprising the steps of:
1) attaching the implant by at least one screw to the bone flap before the bone flap is positioned in the cut-out in the skull in order to avoid putting pressure on the underlying brain while said screw is being attached to the bone flap,
2) placing the implant body in the bore hole,
3) fixing the anchoring wires or plates, preferably by screws and/or sutures or the like, to the surrounding bone and to the bone flap.

In all embodiments of the present invention, depending on the composition of the cement, the hardening of the cement can be performed at reduced, or normal or elevated temperature, and in humid or wet environment. The mould may be made of any dimensionally-stable material which does not react negatively with the cement or mesh/wires. If the mould material is water-permeable it may assist in hardening of the cement.

There are three preferred options regarding the cement moulding:
1. Use (a) a Ca-salt precursor powder composition, and (b) non-aqueous water-miscible liquid. In this case the setting needs to be in a wet environment in order to initiate the hardening.
2. Use (a) a Ca-salt precursor powder composition, and (b) a mixture between water and a non-aqueous water-miscible liquid. Setting will initiate automatically but for final hardening a wet environment is needed.
3. (a) a Ca-salt precursor powder composition, and (b) water-based liquid. Hardening is initiated upon mixing. It is not necessary to perform hardening in a wet environment but hardening could be in a wet environment.

Methods 1 and 2 are preferred because they give a longer working time before the material hardens. This makes it easier to handle the cement and to clean up excess cement after forming the tiles. However too much water in the mixture of method 2 can prevent hardening of the cement and the amount of water in the water/non-aqueous water-miscible liquid mixture should not be more than 50% by weight. The Ca-salt precursor composition may comprise one or more Ca-salts selected from the group consisting of anhydrous dicalcium phosphate, dicalcium phosphate dihydrate, octacalcium phosphate, α-tricalcium phosphate, β-tricalcium phosphate, amorphous calcium phosphate, calcium-deficient hydroxyapatite, non-stoichiometric hydroxyapatite, tetracalcium phosphate and monocalcium phosphate monohydrate (MCPM), anhydrous monocalcium phosphate, phosphoric acid, pyrophosphoric acid, calcium sulphate (alfa or beta, preferably alfa) or calcium silicate (tricalciumsilicate, dicalciumsilicate or monocalcium silicate), calcium carbonate (aragonite, vaterite, calcite or amorphous) or combinations thereof.

In an embodiment of the invention a non-aqueous water-miscible liquid may be used in preparing the pastes. Possible liquids include glycerol and related liquids compounds and derivates (substances derived from non-aqueous water-miscible substances), substitutes (substances where part of the chemical structure has been substituted with another chemical structure) and the like. The purpose of the non-aqueous water-miscible liquid is to give a longer working time during the moulding of the mosaic, because if the material starts to set too early then it is impossible to accurately achieve the mosaic shape.

Certain alcohols may also be suitable for use as such a liquid. Preferably the liquid is selected from glycerol, propylene glycol, poly(propylene glycol), poly(ethylene glycol) and combinations thereof. The composition may also include agents that facilitate a fast diffusion of water into the paste in situ, preferably non-ionic surfactants like Polysorbates. The amount of surfactant is preferably between 0.01 and 5 wt % of the powder composition, most preferably 0.1-1 wt %.

In an alternate embodiment of the present invention the precursor powder composition is chosen to obtain a setting time above about 30 minutes and the liquid can then be water-based or water-containing In this case the liquid can be pure water. In some formulations salts may be dissolved into the liquid to obtain a fast or slower setting, e.g. citric acid, $H_3C_6H_5O_7$, disodium pyrophosphate $Na_2H_2P_2O_7$, sulphuric acid, $H_2SO_4$, phosphoric acid $H_3PO_4$. The hardening can then be performed in a dry environment.

The compositions may also include porogens to give a macroporous end product to facilitate fast resorption and tissue in-growth. The pores give a good foundation for bone cells to grow in. The porogen may include sugars and other fast-resorbing agents. The amount of porogen is suitably between 5 and 30 wt % of the powder composition. This is regardless of whether the composition chosen above is premixed or not.

The compositions may also include a non-toxic gelling agent to enhance cohesiveness and washout resistance. The gelling agent may include collagen, gum, gelatin, alginate, cellulose, polyacrylic acid (e.g. PAA, PAMA), neutral polyacrylic acid (e.g. Na-PAA, Na-PAMA acid), HPMC, HMC and CMC and combinations thereof. The amount of gelling agent preferably represents between 0.1 wt % and 10 wt % of the powder composition, more preferably between 0.1 wt % and 2 wt %. This is regardless of whether the composition chosen above is premixed or not.

In all cement compositions selected above the precursor powder to liquid ratio should preferably be within the range of 1 and 10 as this gives optimal results, and more preferably the ratio is between 3 and 5. Most preferably the powder to liquid ratio is between 3.75 and 4.25. The mean grain size of the precursor powder is preferably below 100 micrometer, and more preferably below 30 micrometer as measured in the volumetric grain size mode. Smaller grain sizes give higher mechanical strength than larger grain sizes. However for the embodiment of the invention containing porous granules the granule size may be larger but preferably is still below about 500 micrometer. Normally granules do not participate in the setting reaction of the paste. They are added as ballast to the material and the presence of pores gives a better biological response to the material. Preferably, at least some of the pores in a granule should be large enough for cells to enter into the granule, normally above at least 10 microns. Inevitably there will also be smaller pores in the granules but they are of less importance for the cell integration.

In another embodiment of a method of manufacturing an implant in accordance with the present invention, in the moulding step a non-aqueous, hydraulic cement composition which comprises a non-aqueous mixture of (a) a Brushite- or Monetite-forming calcium phosphate powder composition, and (b) non-aqueous water-miscible liquid, is moulded onto the wire mesh and allowed to harden in a wet to moist environment.

In another embodiment of a method of manufacturing an implant in accordance with the present invention in the moulding step a non-aqueous, hydraulic cement composition which comprises a non-aqueous mixture of (a) a non-hydrated powder composition comprising porous β-tricalcium phosphate (β-TCP) granules and at least one additional calcium phosphate powder, and (b) non-aqueous water-miscible liquid, is moulded onto the wire mesh and allowed to harden in a wet to moist environment.

One example of a Monetite-forming composition includes a 1:1 molar ratio of β-tricalcium phosphate (preferably with grain size in the range from 0.1 to 100 micrometers) and monocalcium phosphate monohydrate (MCPM), or a 1:1 molar ratio of β-tricalcium phosphate (preferably with grain size in the range from 0.1 to 100 micrometers) and Anhydrous monocalcium phosphate (MCPA). The grain size of MCMP or MCPA may have a larger spread than the β-tricalcium phosphate, and preferably it is in the range from 1 to 800 micrometers. A preferred powder to liquid ratio is in the range of 3 to 5, and the more preferred ratio is between 3.75 and 4.25.

An example of a wet environment is a water bath. An example of a moist environment is a chamber where the relative humidity is 100%. Optionally, hardening of the cement material can be performed at reduced, or normal or elevated temperature, combined with a humid, i.e. a relative humidity over 50%, environment or wet environment.

In an alternate embodiment, the precursor powder composition is basic (apatitic) and comprises (a) a basic calcium phosphate component comprising porous β-TCP granules and tetra calcium phosphate (TTCP) and/or amorphous calcium phosphate, and (b) an acidic phosphate, non-limiting examples of which include monocalcium phosphate monohydrate (MCPM), anhydrous monocalcium phosphate, phosphoric acid, pyrophosphoric acid or combinations thereof. The components of the apatitic precursor powder compositions are chosen such that (i) the pH of the cement paste during setting is higher then 6; and (ii) the end-product of the setting reaction comprises amorphous calcium phosphate hydrate, hydroxyapatite, ion-substituted hydroxyapatite, or combinations thereof.

Once the cement has hardened the cement and wire construction can be removed from the mould, any remaining unwanted cement, for example cement that has fastened onto the wires, is removed and the implant packaged and sterilized.

Optionally the cement and wire construction of the implant system of the present invention could be exposed to pressure during hardening, for example by pressing an inverse mould against the cement, in order to obtain a stronger end product.

The implant system can be attached to the host tissue via sutures and/or plates and screws and/or clamps or any other fixing means.

The implant system can be used in tissue replacements (bone and soft tissue replacement) and in veterinary medicine. For soft tissue replacement the implant structure is preferably composed of polymeric materials, preferably resorbable polymers. For hard tissue the implant system is preferable composed of metal wires and ceramic solids, preferably of metal wires and resorbable ceramics. In the event that the patient is still growing it is appropriate to use resorbable materials for the wires and/or the mosaic plates. Suitable resorbable polymers are Polydioxanone, poly L-lactic acid, and polyglycolic acid.

The implant system may also optionally be combined with an injectable biomaterial or drug delivery vehicle that guides the tissue in-growth into the gaps between the bone and the implant.

While the invention has been illustrated with examples in which an implant in accordance with the present invention is used to fill a bore hole between a bone flap and a surrounding bone, such implants are of course suitable for filling any type of hole when the size and shape of the implant is adapted to the size of the hole to be filled.

The invention is not limited to the embodiments shown, which can be varied freely within the framework of the following claims. In particular, the features of the various embodiments and examples described may be freely combined with each other in order to reach additional embodiments, which are all considered part of the scope of the present application.

The invention claimed is:

1. An implant for filling a bore hole in a bone, comprising:
   a. a single solid ceramic tile body, the tile body having a top surface, a bottom surface, and at least one lateral sidewall extending between the top surface and the bottom surface;
   b. a plurality of wire anchoring arms, each anchoring arm having:
      i. a first portion embedded in the tile body, the ceramic tile body being moulded around the first portions of the wire anchoring arms to provide an internal wire-supported implant body; and
      ii. a second portion extending laterally outwardly from the tile body through a lateral sidewall of the tile body; and
   c. at least two anchoring structures, wherein each anchoring structure is connected to the ceramic tile body by the second portion of a wire anchoring arm, and wherein one of the anchoring structures is positioned for securing the respective anchoring arm to a bone flap and another of the anchoring structures is positioned for securing the respective anchoring arm to surrounding bone structure.

2. The implant of claim 1, comprising more than two wire anchoring arms and more than two anchoring structures.

3. The implant of claim 1, wherein each anchoring structure has an opening adapted to receive a fastener for securing the implant to a bone structure.

4. The implant of claim 1, wherein the implant is sterilized and packaged.

5. The implant of claim 1, wherein the first portions of the anchoring arms are located in a first plane intermediate the top surface and the bottom surface.

6. The implant of claim 1, wherein the second portions of the anchoring arms extend laterally outwardly from the tile body at spaced locations about the at least one lateral sidewall.

7. The implant of claim 6, wherein the anchoring arms are uniformly spaced from each other about the at least one lateral sidewall.

8. The implant of claim 1, wherein the tile body has a circular cross-section and the anchoring arms extend radially outwardly from the lateral sidewall.

9. The implant of claim 8, comprising three or more anchoring arms and three or more anchoring structures.

10. The implant of claim 1, wherein the tile body has a width D between 8 and 20 mm.

11. The implant of claim 10, wherein the width D is between 9 and 15 mm.

12. The implant of claim 10, wherein the width D is between 10 and 14 mm.

13. The implant of claim 1, wherein the tile body has a thickness H between 1 and 10 mm.

14. The implant of claim 13, wherein the thickness H is between 2 and 8 mm.

15. The implant of claim 13, wherein the thickness H is between 3 and 6 mm.

16. The implant of claim 1, wherein the tile body comprises Monetite cement.

17. The implant of claim 1, wherein the tile body comprises Monetite cement formed from (a) β-tricalcium phosphate, and (b) either monocalcium phosphate monohydrate or anhydrous monocalcium phosphate or a mixture thereof.

18. The implant of claim 17, wherein the implant body comprises Monetite cement formed from a 1:1 ratio of (a) and (b).

19. The implant of claim 17, wherein the implant body comprises Monetite cement formed from (a) β-tricalcium phosphate having a grain size in a range of from 0.1 to 100 micrometers, and (b) either monocalcium phosphate monohydrate or anhydrous monocalcium phosphate or a mixture thereof, wherein the grain size of (b) has a spread of from 1 to 800 micrometers.

20. The implant of claim 1, wherein first portions of at least two wire anchoring arms intersect in the ceramic tile body.

21. The implant of claim 1, wherein the tile body has a thickness H between 1 and 6 mm.

22. The implant of claim 1, wherein the tile body has a thickness H between 2 and 6 mm.

23. The implant of claim 1, wherein the anchoring structures are positioned at spaced locations around the perimeter of the ceramic tile body.

24. The implant of claim 1, wherein each second portion of the wire anchoring arms extends not more than 10 mm from the ceramic tile body.

25. The implant of claim 1, wherein each second portion of the wire anchoring arms extends not more than 8 mm from the ceramic tile body.

26. Method of forming an implant according to claim 1, comprising the steps of moulding a cement composition around the first portions of the anchoring arm wires and subsequently allowing said cement composition to cure.

27. The method of claim 26, comprising the steps of: a) providing a mould with at least one cavity having a depth equal to the thickness of the tile body and having the shape of the tile body, wherein each cavity has a closable bottom end and is open at the opposite open end to allow filling of the cavity, wherein the wall of each cavity is pierced by a plurality of wire-retaining channels of width T corresponding with the anchoring arms; b) placing a wire in each wire-retaining channel and extending into the cavity, c) filling said mould with a cement composition; and d) allowing said cement composition to harden.

28. Method according to claim 26, comprising the steps of: i) providing a first mould half with at least one cavity having a depth less than the thickness of the tile body and having the shape of the tile body, wherein each cavity has a closable bottom end and is open at the opposite open end to allow filling of the cavity, ii) filling said first mould half with an excess of cement composition; iii) placing wire anchoring arms over the open end of said cavity and extending laterally outwardly from the cavity; iv) placing a second mould half with a cavity having a depth less than the thickness of the tile body and having the shape of the tile body, arranged as a mirror-image of the first mould half, on top of the wire and compressing the second mould half towards the first mould half; and v) allowing said cement composition to harden.

29. Method of implanting the implant of claim 1 in a bore hole between a bone flap and surrounding bone, comprising the steps of placing the tile body in the bore hole, and fixing one of the anchoring structures to the bone flap and another of the anchoring structures to the surrounding bone.

30. Method according to claim 29, wherein the step of fixing the anchoring structures to the bone flap and surrounding bone is achieved by using sutures, clamps, screws, plates with screws, or a combination thereof.

31. Method according to claim 29, comprising the step of attaching one anchoring structure by at least one screw to the bone flap before the bone flap is positioned in the surrounding bone.

32. An implant for filling a bore hole in a bone, comprising:
  a. a single solid ceramic tile body, the tile body having a top surface, a bottom surface, and one or more lateral sidewalls extending between the top surface and the bottom surface;
  b. a plurality of radially-extending wire anchoring arms, each anchoring arm having:
    i. a first portion embedded in the tile body, the ceramic tile body being moulded around the first portions of the wire anchoring arms to provide an internal wire-supported implant body; and
    ii. a second portion extending laterally outwardly from the tile body through a lateral sidewall of the tile body, wherein the second portions of the respective anchoring arm wires extend laterally outwardly from the tile body at uniformly spaced locations around a perimeter of the tile body; and
  c. a plurality of anchoring structures, wherein each anchoring structure is connected to the ceramic tile body by the second portion of a wire anchoring arm, wherein the anchoring structures are located at uniformly spaced locations around the tile body perimeter, and wherein the anchoring structures comprise screw-receiving openings.

33. The implant of claim 32, wherein two adjacent anchoring structures are connected to each other by a wire segment.

34. The implant of claim 32, wherein the plurality of anchoring arms comprises three or more anchoring arms extending laterally outwardly from the tile body at uniformly spaced locations around the perimeter of the tile body.

35. The implant of claim 32, wherein the plurality of anchoring arms comprises more than three anchoring arms extending laterally outwardly from the tile body at uniformly spaced locations around the perimeter of the tile body.

36. The implant of claim 32, wherein first portions of at least two wire anchoring arms intersect in the ceramic tile body.

37. The implant of claim 32, wherein the tile body has a thickness H between 1 and 6 mm.

38. The implant of claim 32, wherein the tile body has a thickness H between 2 and 6mm.

* * * * *